US011633444B2

(12) United States Patent
Li et al.

(10) Patent No.: US 11,633,444 B2
(45) Date of Patent: Apr. 25, 2023

(54) SPORODERM-REMOVED *GANODERMA LUCIDUM* SPORE POWDER, GRANULE AND PREPARATION METHOD THEREOF (71) Applicants: ZHEJIANG SHOUXIANGU PHARMACEUTICAL COMPANY, LTD, Zhejiang (CN); JINHUA SHOUXIANGU PHARMACEUTICAL CO. LTD, Zhejiang (CN)

(72) Inventors: Zhenhao Li, Zhejiang (CN); Jing Xu, Zhejiang (CN); Ying Wang, Zhejiang (CN); Mingyan Li, Zhejiang (CN); Zhenyu Li, Zhejiang (CN)

(73) Assignees: ZHEJIANG SHOUXIANGU PHARMACEUTICAL COMPANY, LTD, Zhejiang (CN); JINHUA SHOUXIANGU PHARMACEUTICAL CO. LTD, Zhejiang (CN)

( * ) Notice: Subject to any disclaimer, the term of this patent is extended or adjusted under 35 U.S.C. 154(b) by 514 days.

(21) Appl. No.: 16/604,375

(22) PCT Filed: Feb. 6, 2018

(86) PCT No.: PCT/CN2018/075412
§ 371 (c)(1),
(2) Date: Oct. 10, 2019

(87) PCT Pub. No.: WO2018/188409
PCT Pub. Date: Oct. 18, 2018

(65) Prior Publication Data
US 2020/0164011 A1 May 28, 2020

(30) Foreign Application Priority Data
Apr. 10, 2017 (CN) .......................... 201710227611.3

(51) Int. Cl.
*A61K 36/074* (2006.01)
*A23L 31/00* (2016.01)
*A61K 9/14* (2006.01)
*A23L 33/10* (2016.01)

(52) U.S. Cl.
CPC ............ *A61K 36/074* (2013.01); *A23L 31/00* (2016.08); *A23L 33/10* (2016.08); *A23V 2002/00* (2013.01); *A61K 9/14* (2013.01); *A61K 2236/15* (2013.01); *A61K 2236/331* (2013.01); *A61K 2236/37* (2013.01); *A61K 2236/39* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

| CN | 103006728 A | 4/2013 |
|---|---|---|
| CN | 107158043 A | 9/2017 |
| JP | 2000143529 A * | 5/2000 |

OTHER PUBLICATIONS

Li, J.J., et al., Abstract, [Study on variation of main ingredients from spores and fruiting bodies of *Ganoderma lucidum*], China Journal of Chinese Materia Medica, Nov. 1, 2014, 39(21):4246-4251 Language:chi, PMID: 25775802, available at https://europepmc.org/article/med/25775802, accessed on Dec. 10, 2021.*
Soccol, C.R., et al., Pharmacological Properties of Biocompounds from Spores of the Lingzhi or Reishi Medicinal Mushroom *Ganoderma lucidum* (*Agaricomycetes*): A Review, Int'l J of Medicinal Mushrooms, 18(9):757-767 (2016).*
Ma, J., et al., Breaking and Characteristics of Ganoderma Lucidum Spores by High Speed Entrifugal Shearing Pulverizer, J. Wuham Univ. of Technology-Mater. Sci. Ed. Dec. 2007, vol. 22 617-621.*
International Search Report (in Chinese and English) issued in PCT/CN2018/075412, dated Apr. 19, 2018; ISA/CN.

* cited by examiner

*Primary Examiner* — H. Sarah Park
(74) *Attorney, Agent, or Firm* — JCIPRNET (57) ABSTRACT

The present invention discloses sporoderm-removed *Ganoderma lucidum* spore powder, granule and a preparation method thereof. The sporoderm-removed *Ganoderma lucidum* spore powder and granule is obtained from sporoderm-disrupted *Ganoderma lucidum* spore powder through extraction, centrifugation, sporoderm removal, concentration, drying, and pulverization; and in the sporoderm-removed *Ganoderma lucidum* spore powder and granule, the content of polysaccharides is 10-20 g/100 g, and the content of total triterpenes is 4-10 g/100 g. The present invention has beneficial effects of enhancing immunity and having an auxiliary protection function against radiation hazards. The content of active components is increased by processing the sporoderm-disrupted *Ganoderma lucidum* spore powder through a special process, such that the human body can more effectively absorb the nutritional components contained in the *Ganoderma lucidum* spores, and thus the *Ganoderma lucidum* spore powder gives play to its efficacy better while it is convenient to carry and take the *Ganoderma lucidum* spore powder.

10 Claims, 6 Drawing Sheets

SPORODERM-REMOVED *GANODERMA LUCIDUM* SPORE POWDER, GRANULE AND PREPARATION METHOD THEREOF

CROSS REFERENCE TO RELATED APPLICATIONS

The present application is a U.S. National Phase Application under 35 U.S.C. 371 of International Application No. PCT/CN2018/075412 filed on Feb. 6, 2018, which claims priority to Chinese Patent Application No. 201710227611.3 filed to the State Intellectual Property Office on Apr. 10, 2017 and entitled "SPORODERM-REMOVED *GANODERMA LUCIDUM* SPORE POWDER, GRANULE AND PREPARATION METHOD THEREOF". The disclosures of both of the above applications are incorporated herein by reference in their entirety.

TECHNICAL FIELD

The present invention relates to the technical field of medicine and healthcare foods, and more particular to sporoderm-removed *Ganoderma lucidum* spore powder, granule and a preparation method thereof.

BACKGROUND

Human's understanding of the connotation of health concept has been further deepened with the development of science and technology. It has been stated by medical experts of the World Health Organization from more than 50 countries that the best treatment for various diseases is prevention. At present, examinations in the hospitals can only diagnose the diseases that have already occurred. Once the disease is confirmed, it is often too late to cure the disease even with the best means in modern medicine, and is also difficult for the patient to fully recover. The famous ancient Chinese medical text "The Inner Canon of Huangdi" has stated "superior treat before sick, prevention is better than treatment". Superior treat before sick means taking appropriate measures to prevent occurrence and development of a disease, and is a main idea of traditional Chinese medicine. For any disease, the incidence of the disease will be very low, and even completely resolved and avoided, as long as prevention of disease and body maintenance are conducted first. A very important mean for preventing diseases is to enhance the body immunity.

However, the existing health care products regulate immunity generally on the basis of "nourishing", e.g., supplementing various vitamins and amino acids. The health care products may be effective after administration, but the immunity would generally fall back the original level once stopping taking the products, which cannot achieve the effect of fundamentally improving the internal environment of human bodies and improving the immunity.

*Ganoderma lucidum* spores are extremely tiny ovoid germ cells that are ejected from the gills of the fruiting body at its mature period, which is considered as the "seed" of this fungus. It contains the essence of *Ganoderma lucidum*, and is rich in a variety of biologically active substances such as polysaccharides, triterpenoids, proteins, polypeptides, amino acids, nucleoside compounds, organic germanium, trace elements and vitamins. *Ganoderma lucidum* has various activities such as enhancing immunity, resisting radiation and scavenging free radicals with few side effects. However, the spore has a hard sporoderm which is mainly composed of chitin and cellulose, thus is very difficult to be fully absorbed by the body. To improve the absorption of *Ganoderma lucidum* spores, the sporoderm is generally crushed by mechanical crushing methods such as grinding or milling. However, after sporoderm-breaking, it is still difficult for the human body to absorb because a large amount of chitin and cellulose are still in the material, in which the active components still in low levels.

SUMMARY

Aiming at the deficiencies of the prior art, the present invention provides sporoderm-removed *Ganoderma lucidum* spore powder and granules, which can effectively enhance immunity and have an auxiliary protection function against radiation hazards, with high contents of active components such as polysaccharides and total triterpenes, which are easier to absorb. Moreover, the sporoderm-removed *Ganoderma lucidum* spore powder and granules are more convenient to carry and take, enabling the human body to absorb active components more effectively.

The present invention provides sporoderm-removed *Ganoderma lucidum* spore powder and granules, in which granules are produced by using the sporoderm-removed *Ganoderma lucidum* spore powder as the material.

In the sporoderm-removed *Ganoderma lucidum* spore powder and granules, the content of polysaccharides is 10-20 g/100 g, and the content of total triterpenes is 4-10 g/100 g.

Preferably, the particle size of the sporoderm-removed *Ganoderma lucidum* spore powder is less than 0.180 mm.

The present invention provides a method for preparing sporoderm-removed *Ganoderma lucidum* spore powder, including the following steps:

(1) soaking sporoderm-disrupted *Ganoderma lucidum* spore powder, and performing water extraction to obtain an aqueous extract solution of sporoderm-disrupted *Ganoderma lucidum* spores;

(2) concentrating the aqueous extract solution obtained in step (1) to obtain a concentrated solution;

(3) drying the concentrated solution to obtain a dry extract; and (4) pulverizing and then sieving the dry extract to obtain sporoderm-removed *Ganoderma lucidum* spore powder.

Preferably, the soaking is performed in water at a low temperature, and more preferably soaking in water at −5-20° C.; and preferably soaking for 1-4 h, and more preferably soaking for 2 h.

Preferably, water extraction is heating the soaking solution up to 100-120° C. in 10-60 min, and more preferably to 100-120° C. in 30 min.

Preferably, the concentration is performed under reduced pressure ranging from −0.07 to −0.09 MPa, and the temperature is 60-70° C.

Preferably, the drying is microwave drying. The vacuum degree of the microwave drying is −0.07 to −0.09 MPa, and the temperature of the microwave drying is 60-70° C.

The present invention provides a method for preparing sporoderm-removed *Ganoderma lucidum* spore granules, including the following steps: granulating the sporoderm-removed *Ganoderma lucidum* spore powder to obtain the sporoderm-removed *Ganoderma lucidum* spore granules.

Preferably, the granulation is one-step granulation.

Preferably, the one-step granulation includes: mixing the obtained sporoderm-removed *Ganoderma lucidum* spore powder with water, and conducting one-step granulation of the mixture under conditions of a pressure of −2.5 to −3.0

Kpa, an inlet air temperature of 60-80° C., and an outlet air temperature of no more than 60° C.

Preferably, the sporoderm-removed *Ganoderma lucidum* spore granule has a particle size of 12-16 mesh.

The present invention provides a method for preparing the aqueous extract solution of sporoderm-disrupted *Ganoderma lucidum* spores, including the following steps: mixing the sporoderm-disrupted *Ganoderma lucidum* spore powder with water, decocting, and then perform solid-liquid separation, where the mass ratio of the sporoderm-disrupted *Ganoderma lucidum* spore powder to water is 4-6:8-15. Preferably, two times of water extraction is performed, that is, firstly extracting 4-6 parts by weight of the sporoderm-disrupted *Ganoderma lucidum* spore powder with 12 parts by weight of water for 1 time, and filtering to obtain a solution; then decocting the filtered residues with 10 parts by weight of water, and filtering to obtain another solution.

More preferably, three times of water extraction is performed, that is, firstly extracting 4-6 parts by weight of the sporoderm-disrupted *Ganoderma lucidum* spore powder with 12 parts by weight of water, and filtering to obtain a solution; decocting the filtered residues with 10 parts by weight of water for two times, and filtering to obtain two solutions.

Preferably, the water extraction temperature is 80-120° C., and a time period of the water extraction for each time is 1-2 h.

Preferably, after the decoction, the material obtained from the decoction is filtered, and centrifuged to obtain the aqueous extract solution.

Preferably, the temperature of the concentrated solution is 0-4° C., and the centrifugal speed is 2,000-4,000 rpm.

Compared with the prior art, in the present invention, the sporoderm-removed *Ganoderma lucidum* spore powder and granules are prepared by using an aqueous extract of sporoderm-disrupted *Ganoderma lucidum* spore powder as the raw material; and in the present invention, the aqueous extract is obtained by conducting water extraction, concentration, drying and pulverization of the sporoderm-disrupted *Ganoderma lucidum* spore powder. In the product provided by the present invention, the active components of the *Ganoderma lucidum* spores are fully extracted. The chitin and the cellulose shell produced after sporoderm disruption are removed, the contents of the active components are greatly improved, and the product is easier to absorb; the product can comprehensively improve human immunity, including the cellular immune function, the humoral immune function, the monocyte-macrophage function, the NK cell activity, and the like; has an auxiliary protection function against radiation hazards; and has inhibitory effects on each of zebrafish human gastric cancer transplanted tumor, zebrafish human lung adenocarcinoma transplanted tumor and zebrafish human lymphatic cancer transplanted tumor.

Moreover, the product provided by the present invention is in the dosage form of powder and granule, which is convenient to carry and administer, enabling the human body to effectively absorb the nutritional components contained in the *Ganoderma lucidum* spores.

DETAILED DESCRIPTION

The present invention is further described below with reference to the accompanying drawings and embodiments.

The present invention provides sporoderm-removed *Ganoderma lucidum* spore powder and granules, which uses the aqueous extract of sporoderm-disrupted *Ganoderma lucidum* spore powder as the raw material, and granules are produced by using the sporoderm-removed *Ganoderma lucidum* spore powder as the material.

In the sporoderm-removed *Ganoderma lucidum* spore powder and granules, the content of polysaccharides is 10-20 g/100 g, and the content of total triterpenes is 4-10 g/100 g.

The particle size of the sporoderm-removed *Ganoderma lucidum* spore powder and granules provided by the present invention is preferably less than 0.180 mm, and more preferably 0.100-0.160 mm.

The present invention provides a method for preparing sporoderm-removed *Ganoderma lucidum* spore powder, including the following steps:

(1) soaking sporoderm-disrupted *Ganoderma lucidum* spore powder, and performing water extraction to obtain an aqueous extract solution of sporoderm-disrupted *Ganoderma lucidum* spores;

(2) concentrating the aqueous extract solution obtained in step (1) to obtain a concentrated solution;

(3) drying the concentrated solution to obtain a dry extract; and (4) pulverizing and then sieving the dry extract to obtain sporoderm-removed *Ganoderma lucidum* spore powder.

In the present invention, the soaking is preferably soaking in water at a low temperature, and more preferably soaking in water at −5-20° C.; and preferably soaking for 1-4 h, and more preferably soaking for 2 h. Preferably, water extraction and sporoderm removal is heating a soaked solution up to 100-120° C. in 10-60 min, and more preferably to 100-120° C. in 30 min. The sporoderm-disrupted *Ganoderma lucidum* spore powder is subjected to water extraction and solid-liquid separation to obtain an aqueous extract. Water extraction can also sterilize the material. In the present invention, the material, namely the sporoderm-disrupted *Ganoderma lucidum* spore powder can be a commercially-available product, or self-made one (by the inventor). The sporoderm-disruption techniques include mechanical disruption such as vibration mill, supersonic airflow, and shear extrusion. The water extraction is preferably: mixing the sporoderm-disrupted *Ganoderma lucidum* spore powder with water, and then decocting and performing solid-liquid separation to obtain the aqueous extract solution. In the present invention, the mass ratio of the sporoderm-disrupted *Ganoderma lucidum* spore powder to water is preferably 4-6:8-15, and more preferably 5:12.

In the present invention, the water extraction is preferably performed three times. Specifically, the residues obtained by the last decoction are further mixed with water and then sequentially subjected to decoction twice, and the filtrates obtained from the three times of decoction are combined to obtain an extract solution. In the present invention, the time for each time of decoction is preferably 2 h; the filtered residues are decocted in 10 parts by weight of water twice, each time for 2 h, and the solution is filtered out.

In the present invention, the temperature for the water extraction is preferably 80-120° C., and more preferably 90-100° C.; and the time of the water extraction is preferably 1-4 h each time, and more preferably 2 h each time.

In the present invention, after water extraction, the sporoderm removal is realized by the solid-liquid separation, namely filtration of the aqueous extract solution obtained in the extraction procedure. In the present invention, the filtration method is not limited, and is preferably microfiltration membrane filtration or centrifugation. In the present invention, after the aqueous extract solution is obtained, the aqueous extract solution is concentrated to obtain a concentrated solution. In the present invention, the concentration is preferably concentration under reduced pressure. The vacuum degree of the concentration under reduced pressure is preferably −0.07 to −0.09 MPa, and the temperature of the concentration under reduced pressure is preferably 60-70° C. In the present invention, the concentration under reduced pressure is controlled by density, and the density after the concentration under reduced pressure is preferably 1.05-1.15, more preferably 1.08-1.12, and most preferably 1.10.

In the present invention, after concentration, the concentrated solution is dried to obtain a dry extract. In the present invention, the drying method is preferably microwave drying, the vacuum degree of the microwave drying is preferably −0.07 to −0.09 MPa, and the temperature of the microwave drying is preferably 60-70° C.; and preferably, the microwave power is 30 kW. In the present invention, the time of microwave drying is determined by moisture, where the moisture is controlled at preferably 2%-7%, more preferably 3-6%, and most preferably 4%.

In the present invention, after drying, the dry extract is pulverized and then sieved to obtain the aqueous extract of the sporoderm-disrupted *Ganoderma lucidum* spore powder. The pulverization described in the present invention can be a conventional pulverization method in the art. In particular in the embodiment of the present invention, pulverization is conducted by using a pulverizer, and then sieving is conducted to the sieved extract collected; the sieving mesh is preferably 60-100 mesh, and more preferably 80 mesh. In the present invention, after the sporoderm-removed *Ganoderma lucidum* spore powder is obtained, the sporoderm-removed *Ganoderma lucidum* spore powder is granulated to obtain sporoderm-removed *Ganoderma lucidum* spore granules. In the present invention, the granulation is preferably one-step granulation; the granulation is preferably conducted by a boiling granulator; the granulation process is preferably: the sporoderm-removed *Ganoderma lucidum* spore powder is mixed with water, and then subjected to granulation under conditions of a pressure of −2.5 to −3.0 Kpa, an inlet air temperature of 60-80° C., and an outlet air temperature of no more than 60° C.; and more preferably: the fan frequency is set at 26 Hz, and the inlet air temperature is set at 55-60° C., the raw materials are added to the fluidized bed and are heated by hot air moving upwards to keep the materials in a good suspension state. After the materials are mixed for 10 min, the binder (water) passes through a spray system for granulation; the inlet air temperature is set at about 60° C., the material temperature is controlled at 35-55° C.; for atomization pressure, the pressure at the inner layer is 1.5-2.5 kg/cm$^2$ and the pressure at the outer layer is 1.5-2.5 kg/cm$^2$, and the rotation speed of a creep pump is set at 200-250 rpm when the granulation is started, and is set at 150-200 rpm when the particles are gradually formed; after the granulation finishes, the materials are dried, where the inlet air temperature is set at about 80-85° C. and the fan frequency is set at 30-35 Hz, the heating is stopped until the material temperature reaches about 55° C.-60° C., the granulator is stopped when the material temperature is reduced to about 40° C.; and in the granulation workshop, the temperature is controlled at 18° C.-26° C., and the humidity is controlled at 45%-65%.

In the present invention, the particle size prepared by the granulation is 12-16 mesh, and the moisture content is less than 4%; and more preferably, the particle size is 14 mesh.

The technical solutions in the present invention will be clearly and completely described below in conjunction with the embodiments of the present invention. Apparently, the described embodiments are merely a part rather than all of the embodiments of the present invention. All other embodiments obtained by a person of ordinary skill in the art based on the embodiments of the present invention without creative efforts shall fall within the protection scope of the present invention.

EMBODIMENT 1

4 parts by weight of sporoderm-disrupted *Ganoderma lucidum* spore powder was mixed with and soaked in 36 parts by weight of water, and then subjected to water extraction at 80° C. for 2 h. Then the material and the extract solution were centrifuged at 1000 rpm for 15 to 45 min to obtain the first extract solution and the first filter residue; the obtained first filter residue is mixed with 40 parts by weight of water, and then decocted at 99° C. for 2 h, and the same method is used to obtain the second extract solution and the second filter residue; the obtained second filter residue was mixed with 44 parts by weight of water and then decocted at 98° C. for 2 h, and the same method is used to obtain the third extract solution; the first, second and third extract solutions were combined and then concentrated under reduced pressure to a density of 1.15 under conditions of a vacuum degree of −0.08 MPa and a temperature of 60° C., so as to obtain a concentrated solution.

The concentrated solution was subjected to microwave drying under the condition of a vacuum degree of −0.08

MPa and a temperature of 65° C. until the water content reached 6%, so as to obtain a dry extract; the dry extract was pulverized and passed through an 80 mesh sieve to obtain sporoderm-removed *Ganoderma lucidum* spore powder.

In the present invention, after the sporoderm-removed *Ganoderma lucidum* spore powder was obtained, the sporoderm-removed *Ganoderma lucidum* spore powder was mixed with water, and then subjected to 14 mesh granulation under conditions of a pressure of −2.5 Kpa, an inlet air temperature of 60° C., and an outlet temperature of 50° C., so as to obtain sporoderm-removed *Ganoderma lucidum* spore granules.

The contents of polysaccharides and triterpenes of the sporoderm-removed *Ganoderma lucidum* spore powder and granules obtained by the present invention were 15.2 g/100 g and 5.87 g/100 g, respectively, which were much higher than common sporoderm-disrupted *Ganoderma lucidum* spore powder on the market.

EMBODIMENT 2

5 parts by weight of sporoderm-disrupted *Ganoderma lucidum* spore powder was mixed with and soaked in 55 parts by weight of water, and then subjected to water extraction at 80° C. for 2 h, and the aqueous extract was filtered with 1 μm filter membrane to obtain the first extract solution and the first filter residue; the obtained first filter residue was mixed with 50 parts by weight of water, and then decocted at 100° C. for 2 h, and the same method was used to obtain the second extract solution and a second filter residue; the obtained second filter residue was mixed with 60 parts by weight of water and then decocted at 98° C. for 2 h, and the same method is used to obtain the third extract solution; the first, second and third extract solutions were combined and then concentrated under reduced pressure to a density of 1.05 under conditions of a vacuum degree of −0.09 MPa and a temperature of 65° C., so as to obtain a concentrated solution;

The concentrated solution was subjected to microwave drying under the condition of a vacuum degree of −0.07 MPa and a temperature of 70° C. until the water content reached 2%, so as to obtain a dry extract; the dry extract was pulverized and passed through a 60 mesh sieve to obtain the sporoderm-removed *Ganoderma lucidum* spore powder; and In the present invention, after the sporoderm-removed *Ganoderma lucidum* spore powder was obtained, the sporoderm-removed *Ganoderma lucidum* spore powder was mixed with water, and then subjected to 15 mesh granulation under conditions of a pressure of −2.8 Kpa, an inlet air temperature of 65° C., and an outlet temperature of 55° C., so as to obtain sporoderm-removed *Ganoderma lucidum* spore granules.

The contents of polysaccharides and triterpenes of the sporoderm-removed *Ganoderma lucidum* spore powder and granules obtained by the present invention were 15.8 g/100 g and 6.19 g/100 g, respectively, which were much higher than common sporoderm-disrupted *Ganoderma lucidum* spore powder on the market.

EMBODIMENT 3

6 parts by weight of sporoderm-disrupted *Ganoderma lucidum* spore powder was mixed with and soaked in 84 parts by weight of water, and then subjected to water extraction at 80° C. for 2 h, and the plate filtration method is used, namely, the aqueous extract was filtered with 1 μm filter membrane to obtain the first extract solution and the first filter residue; the obtained first filter residue is mixed with 60 parts by weight of water, and then decocted at 99° C. for 2 h, and the same method is used to obtain the second extract solution and a second filter residue; the obtained second filter residue was mixed with 60 parts by weight of water and then decocted at 98° C. for 2 h, and the same method is used to obtain the third extract solution; the first, second and third extract solutions were combined and then concentrated under reduced pressure to a density of 1.10 under conditions of a vacuum degree of −0.09 MPa and a temperature of 70° C., so as to obtain a concentrated solution;

The concentrated solution was subjected to microwave drying under the condition of a vacuum degree of −0.09 MPa and a temperature of 70° C. until the water content reached 3%, so as to obtain a dry extract; the dry extract was pulverized and passed through a 100 mesh sieve to obtain the sporoderm-removed *Ganoderma lucidum* spore powder; and in the present invention, after the sporoderm-removed *Ganoderma lucidum* spore powder was obtained, the sporoderm-removed *Ganoderma lucidum* spore powder was mixed with water, and then subjected to 16 mesh granulation under conditions of a pressure of −3.0 Kpa, an inlet air temperature of 70° C., and an outlet temperature of 60° C., so as to obtain sporoderm-removed *Ganoderma lucidum* spore granules.

The contents of polysaccharides and triterpenes of the sporoderm-removed *Ganoderma lucidum* spore powder and granules obtained by the present invention were 15.4 g/100 g and 6.94 g/100 g, respectively, which were much higher than common sporoderm-disrupted *Ganoderma lucidum* spore powder on the market.

EMBODIMENT 4

Bone-Marrow Nucleated Cell Experiment

The sporoderm-removed *Ganoderma lucidum* spore powder obtained in Embodiment 1 was employed as the Embodiment 1 group, and a negative control group (administrated with deionized water) were set. Mice in each group were subjected to intragastrical administration for 20 days, once a day and each time with a dose of 1.00 g/kg·bw/d, then subjected to 60 Co-γ-ray irradiation. On day 3 after the irradiation a bone marrow nucleated cell experiment was conducted, and the result was shown in Table 1.

TABLE 1

Result of Bone-marrow nucleated cell experiment

| Groups | Number of Animals | Number of hemolysis plaques (number/$10^6$ spleen cells) | Count of bone-marrow nucleated cells ($10^7$/ml) |
|---|---|---|---|
| Negative Control Group | 10 | 95 ± 28 | 1.47 ± 0.31 |
| Embodiment 1 | 10 | 132 ± 23 | 2.01 ± 0.45 |

It could be seen from Table 1 that, the sporoderm-removed *Ganoderma lucidum* spore powder in Embodiment 1 could significantly increase the number of hemolytic plaques and the number of bone marrow nucleated cells, thus improving the cellular immune function, the humoral immune function, the monocyte-macrophage function and the NK cell activity. The result demonstrates that the sporoderm-removed *Ganoderma lucidum* spore powder had an auxiliary protection function against radiation hazards.

Acute toxicity test: the cute toxicity test of the sporoderm-removed *Ganoderma lucidum* spore powder obtained in Embodiment 1 was carried out according to the "Technical Specification for Health Food Inspection and Evaluation" (2003 edition), where the acute oral MTD of female and male mice was greater than 20,000 mg/kg·bw, and the sample belonged to a non-toxic level according to the acute toxicity dose classification standard.

Micronucleus test: the micronucleus test of the sporoderm-removed *Ganoderma lucidum* spore powder obtained in Embodiment 1 was carried out according to the "Technical Specification for Health Food Inspection and Evaluation" (2003 edition), where 3 dose groups of 2.5, 5.0, 10.0 g/kg·bw were set, and the mice were intragastrically administered. The micronucleus test result of the test subject was negative.

Sperm malformation test: the sperm malformation test of the sporoderm-removed *Ganoderma lucidum* spore powder obtained in Embodiment 1 was carried out according to the "Technical Specification for Health Food Inspection and Evaluation" (2003 edition), where 3 dose groups of 2.5, 5.0, 10.0 g/kg·bw were set, and the male mice were intragastrically administered. The sperm malformation test result of the test subject was negative.

Ames test: the Ames test of the sporoderm-removed *Ganoderma lucidum* spore powder obtained in Embodiment 1 was carried out according to the "Technical Specification for Health Food Inspection and Evaluation" (2003 edition), where a plate incorporation method was adopted, and the test doses were respectively of 5,000, 1,000, 200, 40 and 8 μg/dish. The Ames test result of the test subject was negative.

30 days feeding test in rats: the 30 days feeding test of the sporoderm-removed *Ganoderma lucidum* spore powder obtained in Embodiment 1 in rats was carried out according to the "Technical Specification for Health Food Inspection and Evaluation" (2003 edition), where for female rats, 3 dose groups of 4.06, 2.63, 1.18 g/kg·bw/d (equivalent to 122 times, 79 times, and 35 times of the amount recommended for human body) were set; and for male rats, 3 dose groups of 3.79, 2.45, 1.13 g/kg·bw/d (equivalent to 114 times, 74 times, and 34 times of the amount recommended for human body) were set. The test animals were generally in good condition, and had no abnormal change in body weight, food utilization rate, organ weight, and organ coefficient; and hematological and biochemical indicators showed that, all indicators were in the normal range, and no pathological changes associated with the test sample was seen in the histopathological examination of each organ. The experimental results showed that no harmful effect of the sporoderm-removed *Ganoderma lucidum* spore powder was observed from the indicators of all the dose groups in the 30 days feeding test in rats.

It can be seen from the above embodiments that, in the sporoderm-removed *Ganoderma lucidum* spore powder (or granules) of the present invention, the total polysaccharides content was 10-20 g/100 g, and the total triterpenes content was 4-10 g/100 g, such that the sporoderm-removed *Ganoderma lucidum* spore powder and granules of the present invention had an active component content which was greatly improved compared with those of *Ganoderma lucidum* spore powder in the prior art, making the active components be easy to absorb, safe and non-toxic, and be capable of effectively enhancing the body immunity; and the safety of the sporoderm-removed *Ganoderma lucidum* spore powder was also good.

EMBODIMENT 5

Evaluation of Anti-Gastric Cancer Effect of the Sporoderm-Removed *Ganoderma lucidum* Spore Powder And Granules Experimental Animal 1. Wild type AB strain zebrafishes, carried out in a natural paired mating reproduction mode. There were 330 zebrafishes in total, 30 in each experimental group, with the age of 2 days after fertilization (the 330 zebrafishes were used for evaluation of anti-lung adenocarcinoma effect of the sample).

2. Wild type AB strain zebrafishes, carried out in a natural paired mating reproduction mode. There were 480 zebrafishes in total, 30 in each experimental group, with the age of 2 days after fertilization (330 zebrafishes were used for evaluation of anti-lung adenocarcinoma effect of the sample, and 150 zebrafishes were used for a repeated experiment of the evaluation of anti-lung adenocarcinoma effect).

3. Wild type AB strain zebrafishes, carried out in a natural paired mating reproduction mode. There were 660 zebrafishes in total, 30 in each experimental group, with the age of 2 days after fertilization (330 zebrafishes were used for evaluation of anti-lymph cancer effect of the sample, and 330 zebrafishes were used for a repeated experiment of the evaluation of anti-lymph cancer effect of the sample).

The zebrafishes were fed in fish-farming water (water quality: 200 mg of instant sea salt was added per 1 L reverse osmosis water, with a conductivity of 480-510 μS/cm; a pH of 6.9-7.2; and a hardness of 53.7-71.6 mg/L CaCO3) at 28° C., and the experimental animal use license number is: SYXK (Zhejiang) 2012-0171. The feeding management met the requirements of international AAALAC certification.

Experimental Drugs

The sample was sporoderm-removed *Ganoderma lucidum* spore powder, which was brown powder with a lot number 16042301, was soluble in ultrapure water, was dry-stored at room temperature, and was available from Zhejiang Shouxiangu Pharmaceutical Co., Ltd. at May 10, 2016. It was formulated with ultrapure water immediately before use, and was ready for use.

Vincristine sulfate, which was white powder of LOT #K1306055, purchased from Aladdin, and stored in a cool cabinet. Immediately before use, it was formulated with dimethyl sulfoxide (DMSO) into a 5 mM stock solution, and the final working solution had a DMSO concentration of 0.1%.

Cis-platinum, which was yellow powder of LOT #K1520124, purchased from Aladdin, and stored in a cool cabinet. Immediately before use, it was formulated with dimethyl sulfoxide (DMSO) into a 50 mM stock solution, and the final working solution had a DMSO concentration of 0.1%.

Instruments and Reagents

An electronic focusing continuously zoom fluorescence microscope (AZ100, Nikon); a dissecting microscope (SZX7, OLYMPUS, Japan); a camera attached to a microscope (TK-C1481EC); a precision electronic balance (CP214, Ohaus); a 6-well Plate (Nest Biotech); methylcellulose (Aladdin, Shanghai, China).

1. Concentration Groups

| | |
|---|---|
| Experimental group 1 | model control group |
| Experimental group 2 | positive control drug of 50 μM cis-platinum |
| Experimental group 3 | sample of 28 μg/mL |
| Experimental group 4 | sample of 83 μg/mL |
| Experimental group 5 | sample of 250 μg/mL |

2. Basis for Concentration Determination

The MTC of each sample at 35° C. was 250 μg/mL; and according to the project scheme, the sample concentrations for antitumor evaluation were set as: 28 μg/mL (1/9 MTC), 83 μg/mL (1/3 MTC) and 250 μg/mL (MTC).

3. Model Establishment

Human gastric cancer (SGC-7901) cells were labeled with a red fluorescent dye (CM-Dil), and transplanted into zebrafish yolk sacs by microinjection, with about 200 cells being transplanted per zebrafish, so as to establish a zebrafish human gastric cancer transplanted tumor model.

4. Experimental Method

4.1 Determination of Maximum Tolerated Concentration (MTC)

The wild-type AB strain zebrafishes were randomly selected into the 6-well plate, and were respectively given water-dissolved samples at concentrations respectively of 10, 100, 250, 500, 1,000, and 2000 μg/mL, and meanwhile a normal control group was set. During treatment with the test sample, the dead zebrafishes were counted and removed every day; after the zebrafishes were treated with the test sample for 2 days, the movement states and death conditions of the zebrafishes were observed to determine the MTC of the test sample on the zebrafish.

4.2 Evaluation of Anti-Gastric Cancer Effect of the Sample Sporoderm-Removed *Ganoderma lucidum* Spore Powder Human gastric cancer (SGC-7901) cells were labeled with CM-Dil, and transplanted into 2 dpf wild type AB strain zebrafish yolk sacs by microinjection, with about 200 cells being transplanted per zebrafish, so as to establish a zebrafish human gastric cancer (SGC-7901) transplanted model; and the zebrafishes injected with the SGC-7901 cells were fed at 35° C. until 3 dpf.

Zebrafishes with better consistence in transplanted tumor cells were picked out under a microscope, randomly assigned to a 6-well plate, and were given in a water-dissolving administration manner respectively with the samples at concentrations respectively of 28, 83 and 250 μg/mL and the positive control drug cis-platinum at a concentration of 50 μM; and meanwhile a model control group was set, where there were 30 zebrafishes per well (concentration group), and the volume of each well was 5 mL. The zebrafishes in each experiment (concentration) group were continually cultured at 35° C., and after 2 days, 10 zebrafishes were randomly selected from each experiment (concentration) group to observe under a fluorescence microscope, and photographs of the 10 zebrafishes were taken and saved; and the photographs were analyzed using Nikon NIS-Elements D 3.10 Advanced image processing software to calculate the fluorescence intensities of cancer cells. The inhibitory effects of samples on the zebrafish gastric cancer (SGC-7901) transplanted tumor were respectively evaluated with the fluorescence intensities, and the tumor inhibition effect was calculated using the following equation.

$$\text{Tumor inhibition effect (\%)} = \left(1 - \frac{S(\text{Test Sample Group})}{S(\text{Model Control Group})}\right) \times 100\%$$

A concentration-effect curve was drawn according to a growth inhibition effect on the transplanted tumor; statistical analysis was performed by variance analysis and Dunnett's T-test, where $p<0.05$ was considered as a significant difference; such that a representative experimental map was provided.

Special note: the wild-type AB strain zebrafish did not produce red fluorescence itself, and after CM-Dil-labeled cells were injected into zebrafish yolk sacs, red fluorescence can be excited at a certain wavelength, where the sum of fluorescence intensities had positive correlation with the number of cancer cells, and the larger the sum of the fluorescence intensities was, the larger the number of cancer cells was.

5. Experimental Result

5.1 MTC

According to Table 2, when the sample was in the concentration range of 500 μg/mL to 1,000 μg/mL, death occurred in the zebrafishes; and thus it was determined that the MTC of the sample on the zebrafish is 250 μg/mL, and the experiment concentrations for evaluation were all selected as 28 μg/mL (1/9 MTC), 83 μg/mL (1/3 MTC), and 250 μg/mL (MTC).

TABLE 2

"Concentration-mortality" statistical analysis of the test samples

| | Sample 3 | |
|---|---|---|
| Groups | Death Count | Mortality (%) |
| Normal Control Group | 0 | 0 |
| 10 μg/mL | 0 | 0 |
| 100 μg/mL | 0 | 0 |
| 250 μg/mL | 0 | 0 |
| 500 μg/mL | 30 | 100 |
| 1000 μg/mL | 30 | 100 |
| 2000 μg/mL | 30 | 100 |

5.2 Evaluation of Anti-Gastric Cancer Effect of the Sample Sporoderm-Removed *Ganoderma lucidum* Spore Powder For the positive control drug cis-platinum at the concentration of 50 μM, the sum of fluorescence intensity values of the zebrafish human gastric cancer (SGC-7901) transplanted tumor cells was 237,655 pixels, p<0.001 as compared with the model control group (368,978 pixels), and the tumor inhibition effect was 36%, indicating that cis-platinum has a significant inhibition effect on the growth of the zebra fish human gastric cancer (SGC-7901) transplanted tumor.

Figure 1:
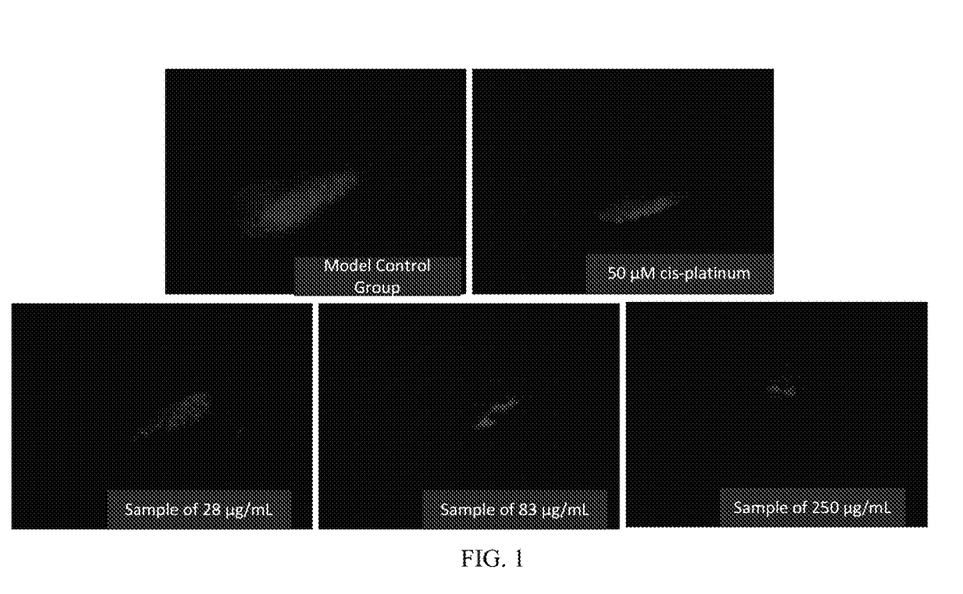
FIG. 1 shows the phenogram of zebrafish treated with the sporoderm-removed *Ganoderma lucidum* spore powder or granule after transplant with human gastric carcinoma tumor (SGC-7901)
Figure 2:
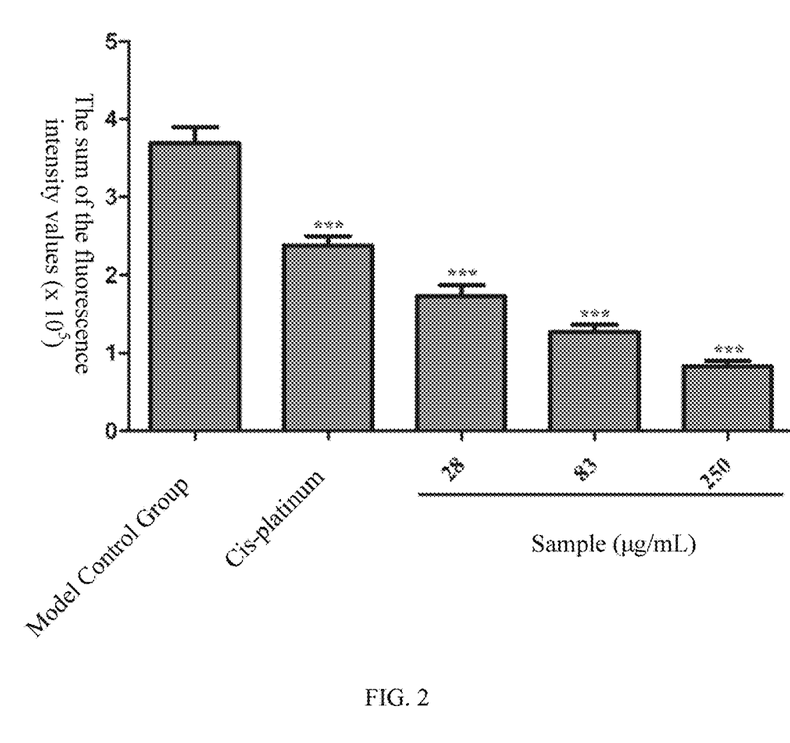
FIG. 2 shows the fluorescence intensity of zebrafish treated with the sporoderm-removed *Ganoderma lucidum* spore powder or granule after transplant with human gastric carcinoma tumor (SGC-7901)
Figure 3:
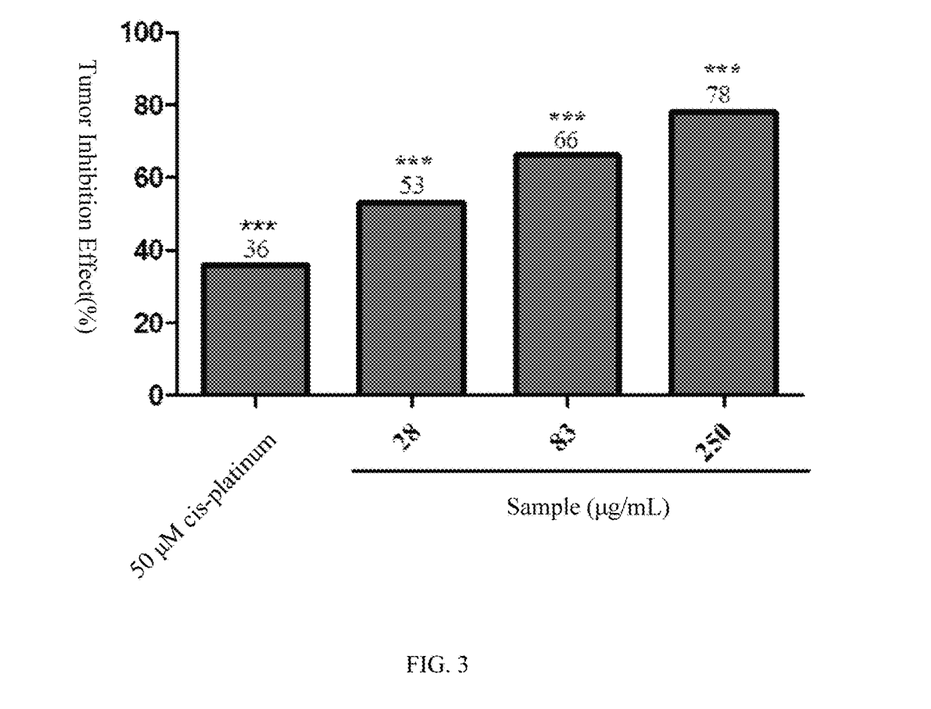
FIG. 3 shows the inhibition effect of the sporoderm-removed *Ganoderma lucidum* spore powder or granule on zebrafish transplanted with human gastric carcinoma tumor (SGC-7901)

When the samples were of the concentrations of 28, 83 and 250 μg/mL, the sums of the fluorescence intensity values of the zebrafish human gastric cancer (SGC-7901) transplanted tumor cells were respectively 173,669, 126,373, and 83,004 pixels, p<0.001 & p<0.001 & p<0.001 as compared with the model control group, and the tumor inhibition effects were respectively 53%, 66%, and 78%. See Table 3, FIG. 1, FIG. 2 and FIG. 3 for details.

TABLE 3

Inhibition effect of samples on zebrafish human gastric cancer (SGC-7901) transplanted tumor (n = 10)

| Experimental Groups | Concentration (μg/mL) | Pixel of Sum of Fluorescence Intensities (mean ± SE) | Inhibition Effect (%) |
|---|---|---|---|
| Model Control Group | — | 368978 ± 20410 | — |
| Cis-platinum | 50 μM | 237655 ± 12361*** | 36*** |
| Sample | 28 | 173669 ± 13570*** | 53*** |
|  | 83 | 126373 ± 9657*** | 66*** |
|  | 250 | 83004 ± 6753*** | 78*** |

Note:
as compared with the model control group,
*p < 0.05,
***p < 0.001

EMBODIMENT 6

Evaluation of Anti-Lymphatic Cancer Effect of the Sporoderm-Removed *Ganoderma lucidum* Spore Powder and Granules 1. Concentration Groups

| | |
|---|---|
| Experimental group 1 | model control group |
| Experimental group 2 | positive control drug of 5 μM vincristine |
| Experimental group 3 | sample of 28 μg/mL |
| Experimental group 4 | sample of 83 μg/mL |
| Experimental group 5 | sample of 250 μg/mL |

2. Basis for Concentration Determination

It was the same as that of Embodiment 5.

3. Model Establishment

Human lymphatic cancer (Ramos) cells were labeled with a red fluorescent dye (CM-Dil), and transplanted into zebrafish yolk sacs by microinjection, with about 200 cells being transplanted per zebrafish, so as to establish a zebrafish human lymphatic cancer transplanted tumor model.

4. Experimental Method

Human lymphatic cancer (Ramos) cells were labeled with CM-Dil, and transplanted into 2 dpf wild type AB strain zebrafish yolk sacs by microinjection, with about 200 cells being transplanted per zebrafish, so as to establish a zebrafish human lymphatic cancer transplanted model; and the zebrafishes injected with the human lymphatic cancer cells were fed at 35° C. until 3 dpf.

Zebrafishes with better consistence in transplanted tumor cells were picked out under a microscope, randomly assigned to a 6-well plate, and were given in a water-dissolving administration manner respectively with the samples at concentrations respectively of 28, 83 and 250 μg/mL and the positive control drug vincristine at a concentration of 5 μM; and meanwhile a model control group was set, where there were 30 zebrafishes per well (concentration group), and the volume of each well was 5 mL. The zebrafishes in each experiment group were continually cultured at 35° C., and after 2 days, 10 zebrafishes were randomly selected from each experiment group to observe under a fluorescence microscope, and photographs of the 10 zebrafishes were taken and saved; and the photographs were analyzed using Nikon NIS-Elements D 3.10 Advanced image processing software to calculate the fluorescence intensities of cancer cells. The inhibitory effect of the sample on the zebrafish lymphatic cancer (Ramos) transplanted tumor was evaluated with the fluorescence intensities, and the tumor inhibition effect was calculated using the following equation.

$$\text{Tumor inhibition effect }(\%) = \left(1 - \frac{S(\text{Test Sample Group})}{S(\text{Model Control Group})}\right) \times 100\%$$

A concentration-effect curve was drawn according to a growth inhibition effect on the transplanted tumor; statistical analysis was performed by variance analysis and Dunnett's T-test, where p<0.05 was considered as a significant difference; such that a representative experimental map was provided.

Special note: the wild-type AB strain zebrafish did not produce red fluorescence itself, and after CM-Dil-labeled cells were injected into zebrafish yolk sacs, red fluorescence can be excited at a certain wavelength, where the sum of fluorescence intensities had positive correlation with the number of cancer cells, and the larger the sum of the fluorescence intensities was, the larger the number of cancer cells was.

5. Experimental Result

For the positive control vincristine at the concentration of 5 μM, the fluorescence intensity of the zebrafish human lymphatic cancer (Ramos) transplanted tumor cells was 153,919 pixels, p<0.001 as compared with the model control group (228,110 pixels), and the tumor inhibition effect was 33%, indicating that vincristine has a significant inhibition effect on the growth of the zebra fish human lymphatic cancer (Ramos) transplanted tumor.

Figure 4:
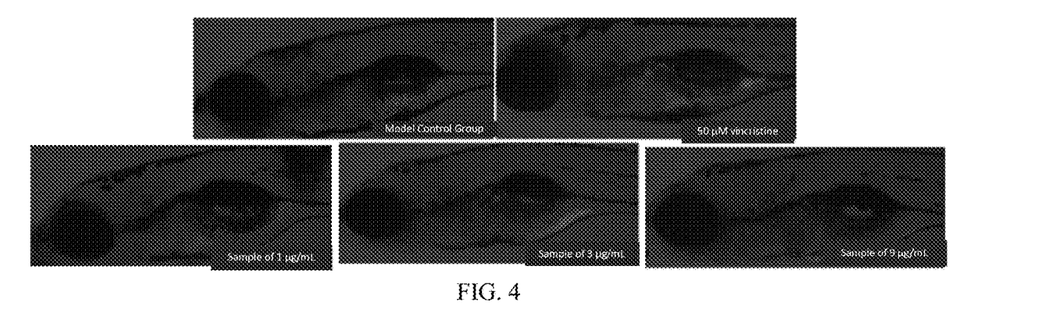
FIG. 4 shows the phenogram of zebrafish treated with the sporoderm-removed *Ganoderma lucidum* spore powder or granule after transplant with human lymphatic cancer (Ramos)
Figure 5:
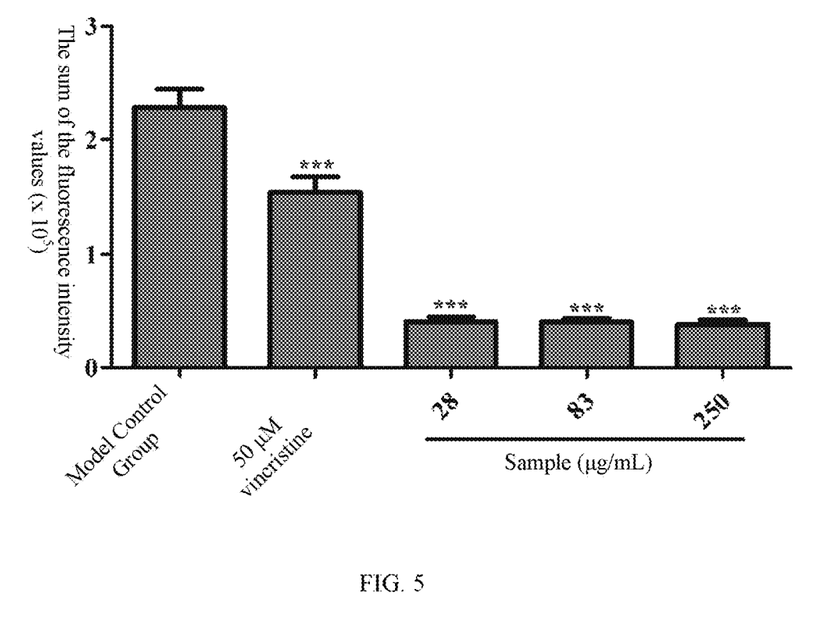
FIG. 5 shows the fluorescence intensity of zebrafish treated with the sporoderm-removed *Ganoderma lucidum* spore powder or granule after transplant with human lymphatic cancer (Ramos)
Figure 6:
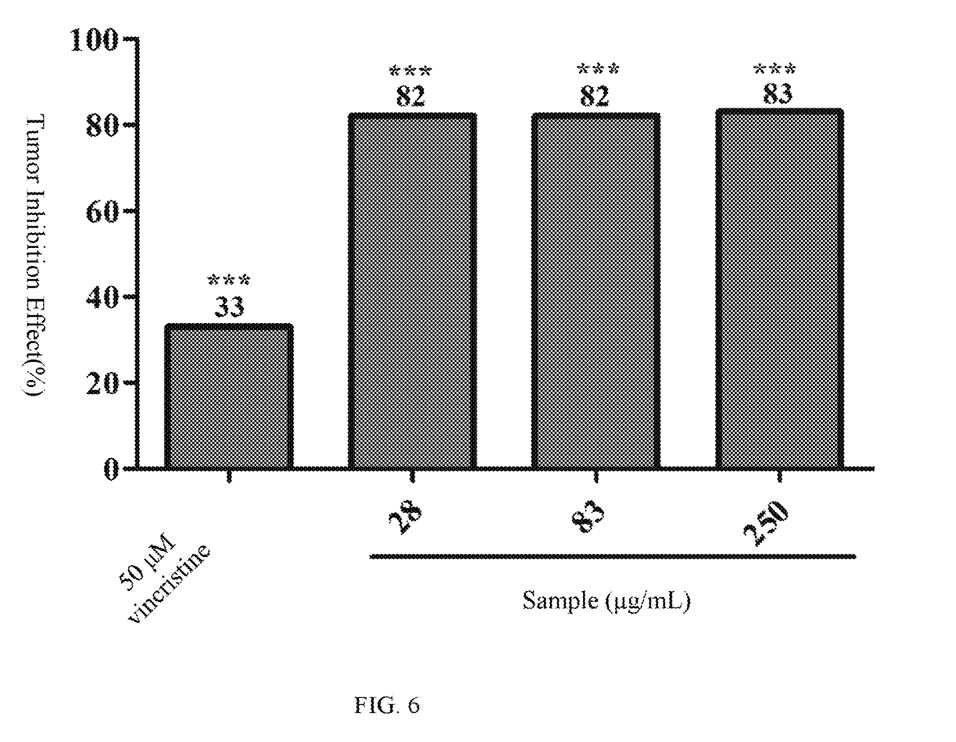
FIG. 6 shows the inhibition effect of the sporoderm-removed *Ganoderma lucidum* spore powder or granule on zebrafish transplanted with human lymphatic cancer (Ramos)

When the samples were of the concentrations of 28, 83 and 250 μg/mL, the sums of the fluorescence intensity values of the zebrafish human lymphatic cancer (Ramos) transplanted tumor cells were respectively 40, 284, 40,166, and 37,884 pixels, for the 3 concentration groups the average p<0.001 as compared with the model control group, and the tumor inhibition effects were respectively 82%, 82%, and 83%. See Table 4, FIG. 4, FIG. 5 and FIG. 6 for details.

TABLE 4

Inhibition effect of sample sporoderm-removed *Ganoderma lucidum* spore powder on zebrafish human lymphatic cancer (Ramos) transplanted tumor (n = 10)

| Experimental Groups | Concentration (μg/mL) | Pixel of Sum of Fluorescence Intensities (mean ± SE) | Inhibition Effect (%) |
|---|---|---|---|
| Model Control Group | — | 228110 ± 15918 | — |
| Vincristine | 5 μM | 153919 ± 13691*** | 33*** |
| Sample | 28 | 40284 ± 4150*** | 82*** |
|  | 83 | 40166 ± 2862*** | 82*** |
|  | 250 | 37884 ± 3789*** | 83*** |

Note:
compared with the model control group,
***$p < 0.001$

EMBODIMENT 7

Evaluation of Anti-Lung Adenocarcinoma Effect of the Sporoderm-Removed *Ganoderma lucidum* Spore Powder and Granules 1. Concentration Groups

| | |
|---|---|
| Experimental group 1 | model control group |
| Experimental group 2 | positive control drug of 50 μM cis-platinum |
| Experimental group 3 | sample of 28 μg/mL |
| Experimental group 4 | sample of 83 μg/mL |
| Experimental group 5 | sample of 250 μg/mL |

2. Basis for Concentration Determination

It was the same as that of Embodiment 5.

3. Model Establishment

Human lung adenocarcinoma (A549) cells were labeled with a red fluorescent dye (CM-Dil), and transplanted into zebrafish yolk sacs by microinjection, with about 200 cells being transplanted per zebrafish, so as to establish a zebrafish human lung adenocarcinoma transplanted tumor model.

4. Experimental Method

Human lung adenocarcinoma (A549) cells were labeled with CM-Dil, and transplanted into 2 dpf wild type AB strain zebrafish yolk sacs by microinjection, with about 200 cells being transplanted per zebrafish, so as to establish a zebrafish human lung adenocarcinoma (A549) transplanted model; and the zebrafishes injected with the A549 cells were fed at 35° C. until 3 dpf.

Zebrafishes with better consistence in transplanted tumor cells were picked out under a microscope, randomly assigned to a 6-well plate, and were given in a water-dissolving administration manner respectively with the samples at concentrations respectively of 28, 83 and 250 μg/mL and the positive control drug cis-platinum at a concentration of 50 μM; and meanwhile a model control group was set, where there were 30 zebrafishes per well (concentration group), and the volume of each well was 5 mL. The zebrafishes in each experiment (concentration) group were continually cultured at 35° C., and after 2 days, 10 zebrafishes were randomly selected from each experiment (concentration) group to observe under a fluorescence microscope, and photographs of the 10 zebrafishes were taken and saved; and the photographs were analyzed using Nikon NIS-Elements D 3.10 Advanced image processing software to calculate the fluorescence intensities of cancer cells. The inhibitory effect of the sample on the zebrafish lung adenocarcinoma (A549) transplanted tumor was evaluated with the fluorescence intensities, and the tumor inhibition effect was calculated using the following equation.

$$\text{Tumor inhibition effect (\%)} = \left(1 - \frac{S(\text{Test Sample Group})}{S(\text{Model Control Group})}\right) \times 100\%$$

A concentration-effect curve was drawn according to a growth inhibition effect on the transplanted tumor; statistical analysis was performed by variance analysis and Dunnett's T-test, where $p<0.05$ was considered as a significant difference; such that a representative experimental map was provided.

Special note: the wild-type AB strain zebrafish did not produce red fluorescence itself, and after CM-Dil-labeled cells were injected into zebrafish yolk sacs, red fluorescence can be excited at a certain wavelength, where the sum of fluorescence intensities had positive correlation with the number of cancer cells, and the larger the sum of the fluorescence intensities was, the larger the number of cancer cells was.

5. Experimental Result

Figure 7:
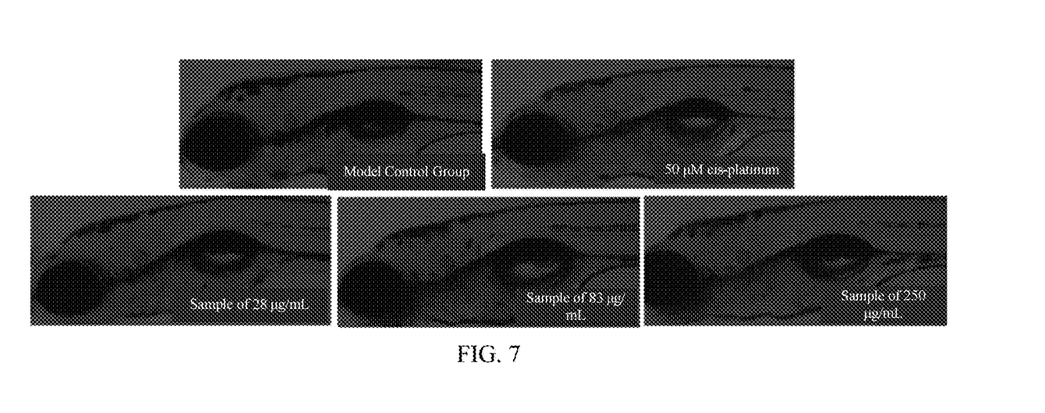
FIG. 7 shows the phenogram of zebrafish treated with the sporoderm-removed *Ganoderma lucidum* spore powder or granule after transplant with human lung adenocarcinoma (A549)
Figure 8:
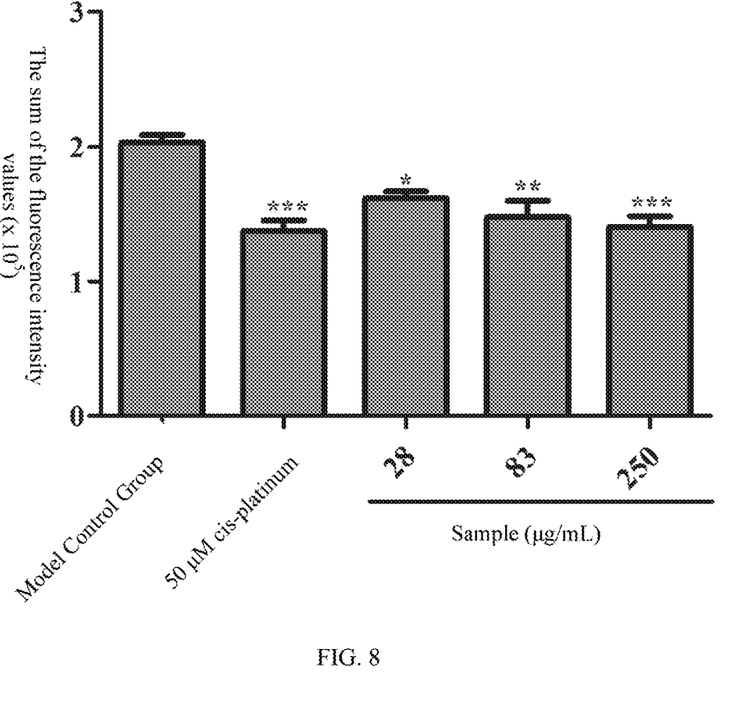
FIG. 8 shows the fluorescence intensity of zebrafish treated with the sporoderm-removed *Ganoderma lucidum* spore powder or granule after transplant with human lung adenocarcinoma (A549)
Figure 9:
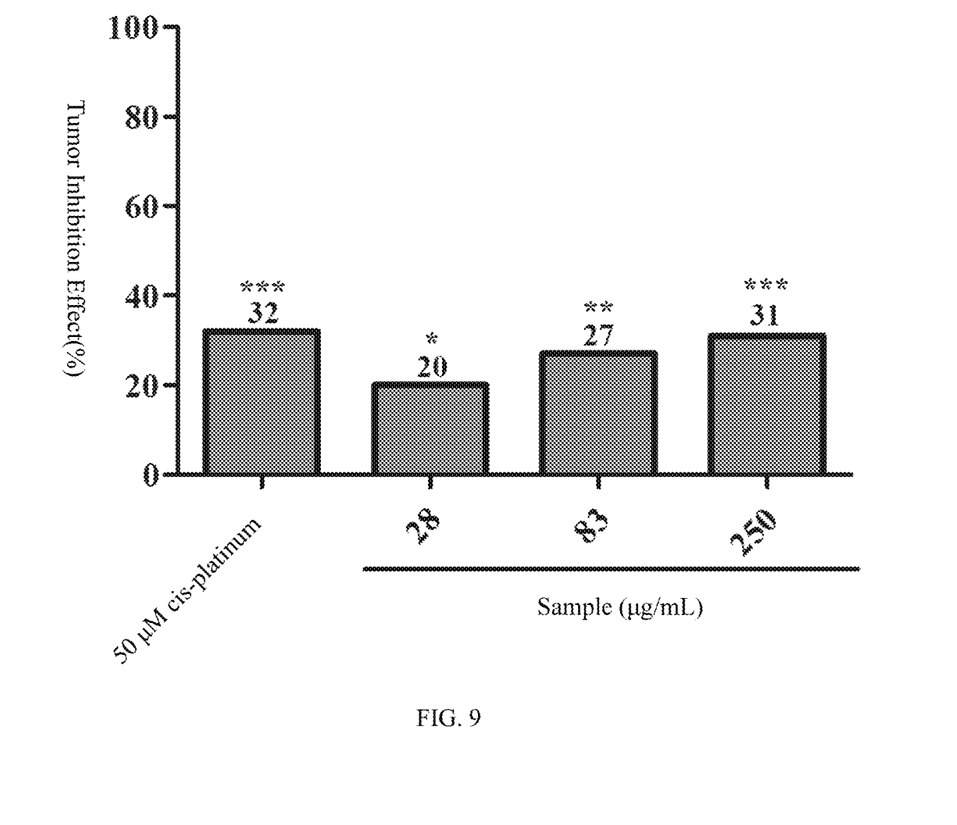
FIG. 9 shows the inhibition effect of the sporoderm-removed *Ganoderma lucidum* spore powder or granule on zebrafish transplanted with human lung adenocarcinoma (A549)

For the positive control drug cis-platinum at the concentration of 50 μM, the sum of fluorescence intensity values of the zebrafish human lung adenocarcinoma (A549) transplanted tumor cells was 137,287 pixels, p<0.001 as compared with the model control group (203,330 pixels), and the tumor inhibition effect was 32%, indicating that cis-platinum has a significant inhibition effect on the growth of the zebra fish human lung adenocarcinoma (A549) transplanted tumor. When the samples were of the concentrations of 28, 83 and 250 μg/mL, the sums of the fluorescence intensity values of the zebrafish human lung adenocarcinoma (A549) transplanted tumor cells were respectively 161,737, 147,640, and 140,415 pixels, for the group of 28 μg/mL p<0.05 as compared with the model control group, and the tumor inhibition effect was 20%; for the group of 83 μg/mL p<0.01 as compared with the model control group, and the tumor inhibition effect was 27%; and for the group of 250 μg/mL p<0.001 as compared with the model control group, and the tumor inhibition effect was 31%. See Table 5, FIG. 7, FIG. 8 and FIG. 9 for details.

TABLE 5

Inhibition effect of sample sporoderm-removed *Ganoderma lucidum* spore powder on zebrafish human lung adenocarcinoma (A549) transplanted tumor (n = 10)

| Experimental Groups | Concentration (μg/mL) | Pixel of Sum of Fluorescence Intensities (mean ± SE) | Inhibition Effect (%) |
|---|---|---|---|
| Model Control Group | — | 203330 ± 5548 | — |
| Cis-platinum | 50 μM | 137287 ± 7835** | 32*** |
|  | 28 | 161737 ± 4965* | 20* |

TABLE 5-continued

Inhibition effect of sample sporoderm-removed *Ganoderma lucidum* spore powder on zebrafish human lung adenocarcinoma (A549) transplanted tumor (n = 10)

| Experimental Groups | Concentration (μg/mL) | Pixel of Sum of Fluorescence Intensities (mean ± SE) | Inhibition Effect (%) |
|---|---|---|---|
| Sample | 83 | 147640 ± 12154** | 27** |
|  | 250 | 140415 ± 7801*** | 31*** |

Note:
as compared with the model control group,
*p < 0.05,
**p < 0.01,
***p < 0.001

The test results show that: under the test condition of this experiment, the sporoderm-removed *Ganoderma lucidum* spore powder and granule of the present invention have inhibitory effects on the zebrafish human gastric cancer transplanted tumor, the zebrafish human lung adenocarcinoma transplanted tumor and the zebrafish human lymphatic cancer transplanted tumor, where the inhibitory effects on the zebrafish human gastric cancer transplanted tumor and zebrafish human lymphatic cancer transplanted tumor are stronger.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for preparing a powder of sporoderm-removed *Ganoderma lucidum* spore, comprising the steps of:
    (1) soaking a powder of sporoderm-disrupted *Ganoderma lucidum* spore, and performing water extraction to obtain an aqueous extract solution of sporoderm-disrupted *Ganoderma* lucidumspore, wherein a sporoderm of sporoderm-disrupted *Ganoderma lucidum* spore is removed after performing the water extraction;
    (2) concentrating the aqueous extract solution obtained in step (1) to obtain a concentrated solution;
    (3) drying the concentrated solution to obtain a dry extract; and
    (4) pulverizing and then sieving the dry extract to obtain the powder of sporoderm-removed *Ganoderma lucidum* spore;
    wherein
    a content of polysaccharides in the powder of sporoderm-removed *Ganoderma lucidum* spore is 10-20 g/100 g, and a content of total triterpenes in the powder of sporoderm-removed *Ganoderma lucidum* spore is 4-10 g/100 g,
    wherein the water extraction in step (1) is performed 2-3 times, a water extraction temperature is 80-120° C., and a time period of the water extraction is 4-6 h;
    wherein the water extraction in step (1) comprises: firstly mixing 4-6 parts by weight of the powder of sporoderm-disrupted *Ganoderma lucidum* spore with 12 parts by weight of water for 1 time to form a first solution, and filtering the first solution to obtain a first extract solution and a first filtered residue; decocting the first filtered residue with 10 parts by weight of water for 1-2 times to form a second solution, and filtering the second solution to obtain a second extract solution and a second filtered residue; and combining the first extract solution and the second extract solution to obtain the aqueous extract solution, and
    wherein filtering the first solution comprises a step of first centrifugation to separate the first filtered residue from the first extract solution, and filtering the second solution comprises a step of second centrifugation to separate the second filtered residue from the second extract solution.

2. The method of claim 1, wherein a mass ratio of the powder of sporoderm-disrupted *Ganoderma lucidum* spore to water is 4-6:8-15 when mixing the powder of sporoderm-disrupted *Ganoderma lucidum* spore with water.

3. The method of claim 2, further comprising:
    granulating the powder of sporoderm-removed *Ganoderma lucidum* spore to form a granule of sporoderm-removed *Ganoderma lucidum* spore, wherein the granulating is performed as follows: mixing the powder of sporoderm-removed *Ganoderma lucidum* spore with water to obtain a mixture, and subjecting the mixture to a one-step granulation under conditions of a pressure of −2.5 to −3.0 Kpa, an inlet air temperature of 60-80° C., and an outlet air temperature of no more than 60° C.

4. The method of claim 2, wherein during the first centrifugation, a temperature of the first solution is 0-4° C., and a centrifugal speed in the first centrifugation is 2,000-4,000 rpm, and during the second centrifugation, a temperature of the second solution is 0-4° C., and a centrifugal speed in the second centrifugation is 2,000-4,000 rpm.

5. The method of claim 4, further comprising:
    granulating the powder of sporoderm-removed *Ganoderma lucidum* spore to form a granule of sporoderm-removed *Ganoderma lucidum* spore, wherein the granulating is performed as follows: mixing the powder of sporoderm-removed *Ganoderma lucidum* spore with water to obtain a mixture, and subjecting the mixture to a one-step granulation under conditions of a pressure of −2.5 to −3.0 Kpa, an inlet air temperature of 60-80° C., and an outlet air temperature of no more than 60° C.

6. The method of claim 1, wherein in step (2), the concentrated solution is a concentration under reduced pressure, a vacuum degree of the concentration under reduced pressure is −0.07 to −0.09 MPa, and a temperature of the concentration under reduced pressure is 60-70° C.;
    wherein in step (3), the drying is microwave drying, a vacuum degree of the microwave drying is −0.07 to −0.09 MPa, and a temperature of the microwave drying is 60-70° C.; and a time of the microwave drying is controlled by moisture, wherein the moisture is controlled at 2%-7%.

7. The method of claim 6, further comprising:
    granulating the powder of sporoderm-removed *Ganoderma lucidum* spore to form a granule of sporoderm-removed *Ganoderma lucidum* spore, wherein the granulating is performed as follows: mixing the powder of sporoderm-removed *Ganoderma lucidum* spore with water to obtain a mixture, and subjecting the mixture to a one-step granulation under conditions of a pressure of −2.5 to −3.0 Kpa, an inlet air temperature of 60-80° C., and an outlet air temperature of no more than 60° C.

8. The method of claim 1, wherein a density of the concentrated solution in step (2) is 1.05-1.15.

9. The method of claim 1, further comprising:
granulating the powder of sporoderm-removed *Ganoderma lucidum* spore to form a granule of sporoderm-removed *Ganoderma lucidum* spore after pulverizing and sieving.

10. The method of claim 9, wherein the granulating is performed as follows: mixing the powder of sporoderm-removed *Ganoderma lucidum* spore with water to obtain a mixture, and subjecting the mixture to a one-step granulation under conditions of a pressure of −2.5 to −3.0 Kpa, an inlet air temperature of 60-80° C., and an outlet air temperature of no more than 60° C.

* * * * *